United States Patent [19]

Lindenbaum et al.

[11] 4,143,131
[45] Mar. 6, 1979

[54] REMOVAL OF PLUTONIUM FROM HEPATIC TISSUE

[75] Inventors: Arthur Lindenbaum, Lockport; Marcia W. Rosenthal, La Grange, both of Ill.

[73] Assignee: The United States of America as represented by the United States Department of Energy, Washington, D.C.

[21] Appl. No.: 546,851

[22] Filed: Mar. 29, 1974

[51] Int. Cl.$^2$ ............................................. A61K 45/02
[52] U.S. Cl. .......................................... 424/85; 424/2; 424/10
[58] Field of Search ................................ 424/85, 10, 2

[56] References Cited

PUBLICATIONS

C.A. 73, #771j (1970), Sanders et al.
C.A. 74, #51701q (1971), Regelson et al.
C.A. 81, #150137m (1974), Khaijovich et al.
C.A. 81, #60109z (1974), Talas et al.
Chemical Abstracts, vol. 77, entry 1 09858b, 1972.
Rosenthal et al., Radiation Research, vol. 53, No. 1, pp. 102–114, 1973.

*Primary Examiner*—Shep K. Rose
*Attorney, Agent, or Firm*—Dean E. Carlson; Frank H. Jackson; Robert J. Fisher

[57] ABSTRACT

A method is provided for removing plutonium from hepatic tissues by introducing into the body and blood stream a solution of the complexing agent DTPA and an adjunct thereto. The adjunct material induces aberrations in the hepatic tissue cells and removes intracellularly deposited plutonium which is normally unavailable for complexation with the DTPA. Once the intracellularly deposited plutonium has been removed from the cell by action of the adjunct material, it can be complexed with the DTPA present in the blood stream and subsequently removed from the body by normal excretory processes.

4 Claims, No Drawings

REMOVAL OF PLUTONIUM FROM HEPATIC TISSUE

CONTRACTUAL ORIGIN OF THE INVENTION

The invention described herein was made in the course of, or under, a contract with the UNITED STATES ATOMIC ENERGY COMMISSION.

BACKGROUND OF THE INVENTION

This invention relates to a method for removing plutonium from the body and more particularly is directed toward a method for removing polymeric plutonium from hepatic tissue.

Continuing studies have been directed toward development of new approaches to the therapy of poisoning by both nonradioactive and radioactive metals. Considerable emphasis has been directed in the last several years toward the radioactive elements in view of the radiological health hazards they present. The ionizing radiations of the radioactive metals are of even greater concern than their chemical toxicity because of the risk of pathological changes and tumor induction from the radioactive ionizations. Compounds of toxic heavy metals are known to preferentially concentrate in various organs of the body. For example, plutonium introduced into the blood becomes selectively deposited mainly in the liver (as much as 30% to 90% of an administered amount of plutonium) and in the skeleton. Once the toxic metal has deposited within an organ its concentration may be only very slowly reduced, thereby increasing the potential for tumors and other radiation-induced damage. Plutonium deposited in the skeleton is of particular concern because of its high potential for inducing the formation of delayed osteogenic sarcomas. Plutonium deposited in the liver poses an additional problem, as a large fraction of the deposited plutonium which slowly leaves this organ may be translocated to bone surfaces, at which location its toxicity is much enhanced.

Previous techniques have employed the polyaminopolycarboxylic acid ethylenediaminetetraacetic acid (EDTA) as a chelating agent for removing toxic metals from animal tissue. More recently, a related polyaminopolycarboxylic acid, diethylenetriaminepentaacetic acid (DTPA) has been shown to have a greater ability to remove various heavy metals, particularly plutonium and other actinide elements. The use of these chelating agents, usually in the form of their calcium and/or sodium salts, for the removal of toxic metals is based on their ability to form stable, soluble, and readily excretable complexes with the metal ions in the tissues. They have proven valuable because they, in themselves, have a very low toxicity, are soluble, and resist degradation by tissue metabolites. However, a serious limitation to the use of chelating agents such as DTPA and EDTA is that they exist as charged, hydrated, lipid-insoluble anions in the blood plasma. These anions are unable to penetrate cellular membranes. Therefore, only extracellularly deposited metals are accessible for complexation by the chelating agent and subsequent removal from the body, whereas intracellularly deposited metals are not accessible to the chelating agent and therefore are not readily removed.

More recent attention, therefore, has been directed toward finding substances which will be effective in removing intracellularly deposited toxic metals, plutonium in particular. One substance which we have demonstrated as being effective in removal of additional plutonium, and in particular hepatic plutonium otherwise unavailable for chelation by DTPA, is the polysaccharide glucan derived from yeast cell walls. Glucan, however, is not totally satisfactory since glucan is insoluble and exhibits toxicity, factors which must be taken into account in the development of any practical therapeutic technique.

Therefore, it is an object of the present invention to provide a method for removing plutonium from the body.

It is another object of the present invention to provide a method for removing intracellularly deposited plutonium.

Another object of the present invention is to provide a method for removing plutonium from hepatic tissues.

It is another object of the present invention to provide a method for removing hepatic plutonium not removable by chelating agents alone.

Another object of the present invention is to provide a method for removing plutonium from hepatic tissues and from the body without translocating the plutonium to other tissues.

SUMMARY OF THE INVENTION

In accordance with the present invention, plutonium is removed from hepatic tissue and the body by introducing into the body and blood stream a solution of DTPA and an adjunct thereto which will cause the plutonium deposited in the hepatic tissue to be removed from this tissue and thereby made available for complexation by the DTPA exterior to the cells and in the blood stream. The complexed plutonium can then be removed from the body by the normal body processes. It has been found that certain soluble substances, known to induce the formation of intracellular polysaccharide-containing inclusions in the liver, can also function to remove hepatic plutonium otherwise unavailable to the action of DTPA, thereby making it available for chelation and subsequent removal from the body. Other features of the invention will become apparent upon reading the following detailed description.

DETAILED DESCRIPTION OF THE INVENTION

Since the use of DTPA is a proven therapeutic method and DTPA is known to be very efficient in complexing and removing from the body any plutonium which is accessible to it, efforts were directed toward finding materials which would cause intracellularly deposited plutonium, which is normally unavailable to the DTPA for complexation, to be ejected from the cell and thereby made available to the DTPA for subsequent complexation and ultimate removal from the body. Particular attention was directed towards hepatic tissues, although similar tissues of the reticuloendothelial type in other organs may exhibit reactions similar to those observed in the liver. Tests were conducted in mice to determine materials and types of materials which would render intracellularly deposited plutonium available to the subsequent action of DTPA by inducing removal of the plutonium from the cell. Results of some of these tests are indicated in the following table which shows the removal of plutonium from mouse liver in terms of the percent of the injected plutonium remaining in the liver forty-seven days after injection of the plutonium.

| Removal of Polymeric Plutonium From Mouse Liver | |
|---|---|
| Treatment | % Injected Pu Remaining in Liver (47 days post Pu) |
| Control | 34 |
| DTPA | 31 |
| Pyran Copolymer + DTPA | 16 |
| Isosclerotan + DTPA | 20 |
| Glucan + DTPA | 20 |
| Tilorone + DTPA | 23 |

In each of the cases indicated in the table, the treatment material was administered intravenously to mice which had been injected intravenously with "mid-range" polymeric plutonium five days previously. The treatment material was introduced in conjunction with DTPA therapy, the latter being continued thereafter at a dosage of 100 mg/kg of body weight administered twice weekly. A polymeric form of plutonium was employed in these tests in order to increase the fraction of injected plutonium deposited within the hepatic tissue. Plutonium when introduced into the body and blood stream, in monomeric form will polymerize with time. The liver tissue preferentially takes up polymeric plutonium over monomeric plutonium; also it has been found that polymeric plutonium is deposited intracellularly whereas monomeric plutonium remains extracellular to a large extent. Therefore use of polymeric plutonium increases the fraction of hepatic plutonium and intracellular plutonium, thus facilitating study of plutonium deposited in organs like the liver. For each of the treatments shown in the table, five or six animals were used, and the numbers in the table are averages for the five or six animals used in each case. Dosage of the compound used for the adjunct therapy was between 25 and 100 mg of substance per kg of body weight, with 100 mg per kg body weight of DTPA also being used for each such injection. The DTPA and the adjunct material were introduced by an intravenous injection five to six days after plutonium administration. Intravenous injection is preferred as it immediately introduces the material into the blood stream. However, removal of plutonium by introduction of the adjunct via an intraperitoneal injection or oral administration may also be possible. Therapy treatment with DTPA was continued twice weekly for 47 days after plutonium injection at which time the mice were sacrificed.

As indicated in the table, the four tested adjuncts to DTPA therapy removed significant additional plutonium from the liver. As can be seen, a control group which received no therapy retained 34% of the injected plutonium after 47 days. DTPA used alone resulted in a retention of 31% whereas the other four materials used as adjuncts to the DTPA therapy resulted in retention of only from 16% to 23% of the plutonium. Pyran copolymer proved to be the most effective material when used in conjunction with a solution of DTPA. The particular pyran copolymer used in obtaining the results listed in the table is a condensation product of maleic acid and divinyl ether and can be further described as a divinyl ether maleic anhydride copolymer typically having an approximate peak height molecular weight between 22,000 and 33,000. Another similar pyran copolymer also has been found to be effective. In this particular case, the pyran copolymers used were obtained from Hercules Incorporated.

The compound designated Tilorone in the table is one of a series of related compounds available from Richardson-Merrell, Inc. listed under the name Tilorones. The particular Tilorone which was used in obtaining the results in the table has a Richardson-Merrell designation Tilorone RMI-10,028 DA and its chemical identity is 2,7-bis[2-(diethylamino)ethoxy] fluoren-9-one dihydrochloride or Tilorone dihydrochloride. Other Tilorones and compounds of a similar structure and related derivatives of 9-fluorenone are also believed to be effective.

Both the Tilorones and the pyran copolymers are interferon inducers. The term "interferon inducer" indicates a material which will stimulate the production of interferons in a cell. These materials also could be referred to as anti-viral agents because of their ability to counteract viral infections. These materials are preferred in the practice of the present invention for several reasons. These materials are soluble in a saline solution or the blood stream and therefore avoid any problem which could arise from injecting a colloid or particle suspensions of some sort into the blood steam. When administered in conjunction with DTPA, these materials remove the plutonium from the liver without introducing a potential for translocation of the plutonium to bone tissue. Other materials also tested for effectiveness in removing plutonium from the hepatic tissues were poly I/C, a synthetic polynucleotide, Triton® WR 1339, a wetting agent from Rohm & Haas Co. known to affect intracellular inclusions termed lysosomes, as well as bacterial cell wall polysaccharides extracted from the microorganism *Bacillus subtilis*. However, these latter materials did not prove to be effective. Isosclerotan is an insoluble glucopolysaccharide and is a constituent of fungal cell walls. This particular material was investigated as it is somewhat analogous to glucan, which is an insoluble polysaccharide derived from yeast cell walls. It was believed that if isosclerotan also proved to be effective it would assist in determining the mechanism of the removal of the plutonium from the interior of the cell.

A correlation has been found between these compounds which apparently is related to their effectiveness in removing plutonium from the liver. Both the pyran copolymer and Tilorone induce cellular changes of a type which may have a role in the subsequent removal of plutonium from the cell. Each of these substances are known to affect the hepatic tissue in a manner which results in the formation of polysaccharide-containing intracellular inclusions. On the basis of this evidence as well as other evidence of intracellular incorporation of polymeric plutonium, an effective adjunct material is apparently one which will induce the hepatic tissue to produce therein intracellular polysaccharide-containing inclusions with the result that, by a process as yet not fully defined, the tissue itself is stimulated to eject the intracellularly deposited plutonium. The soluble interferon inducers are thus assumed to be a class of preferred adjuncts for removal of intracellularly deposited plutonium, with the pyran copolymer giving the best results of the tested interferon inducers.

These materials are employed as adjuncts to the DTPA and result in the removal of plutonium which was otherwise not available for removal by the DTPA itself. In particular, plutonium in hepatic tissues not removable by DTPA is removed by these materials from the hepatic tissue to extracellular spaces where it is available for complexation by the DTPA. The complexed plutonium can then be removed from the blood and ultimately flushed from the body by normal excretory processes.

The embodiments of the invention in which an exclusive property or privilege is claimed are defined as follows:

1. A method for removing intracellulary deposited plutonium from hepatic tissue comprising: introducing into the body and blood stream a solution of DTPA and introducing as an adjunct thereto a pyran copolymer, whereby the plutonium is removed from the hepatic tissue and is removed from the body by the normal body processes.

2. The method in accordance with claim 1 wherein said pyran copolymer is a condensation product of maleic acid and divinyl ether.

3. The method of claim 2 wherein said pyran copolymer is a divinyl ether maleic anhydride copolymer having an approximate molecular weight between 22,000 and 33,000.

4. The method of claim 1 wherein said DTPA solution and said adjunct are introduced into the body by intravenous injection.

* * * * *